US012714311B2

(12) United States Patent
Brace et al.

(10) Patent No.: US 12,714,311 B2
(45) Date of Patent: Aug. 25, 2026

(54) MAGNETIC RESONANCE ELASTOGRAPHY SYSTEM FOR THE PROSTATE

(71) Applicant: Wisconsin Alumni Research Foundation, Madison, WI (US)

(72) Inventors: Christopher Brace, Madison, WI (US); Shane Wells, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 0 days.

(21) Appl. No.: 18/636,539

(22) Filed: Apr. 16, 2024

(65) Prior Publication Data

US 2025/0318730 A1 Oct. 16, 2025

(51) Int. Cl.
*A61B 5/00* (2006.01)
*A61B 5/055* (2006.01)

(52) U.S. Cl.
CPC ............ *A61B 5/0053* (2013.01); *A61B 5/055* (2013.01); *A61B 5/4381* (2013.01)

(58) Field of Classification Search
None
See application file for complete search history.

(56) References Cited

U.S. PATENT DOCUMENTS

2012/0053450 A1* 3/2012 Salcudean ............ A61B 5/0051 600/421
2016/0274210 A1* 9/2016 Sack ...................... A61B 5/055
2020/0341098 A1* 10/2020 Murphy ............. G01R 33/5608

OTHER PUBLICATIONS

Jock, "Jockstrap," (Mar. 30, 2024), <https://en.wikipedia.org/w/index.php?title=Jockstrap&oldid=1216357350>, retrieved on May 30, 2025. (Year: 2024).*

Jin Wang et al.; "New and emerging applications of magnetic resonance elastography of other abdominal organs." Topics in Magnetic Resonance Imaging 27, available in PMC; No. 5 (Oct. 2018): pp. 1-37.

S.A. Kruse et al.; "Tissue characterization using magnetic resonance elastography: preliminary results." Physics in Medicine & Biology 45, No. 6 (2000): pp. 1579-1590. UK.

Kenneth Hoyt et al.; "Tissue elasticity properties as biomarkers for prostate cancer." Cancer Biomarkers 4, No. 4-5 (2008): pp. 1-23. US.

EC Ehman et al.; "Vibration safety limits for magnetic resonance elastography." Physics in Medicine & Biology 53, No. 4 (2008): pp. 1-16. US.

Mikio Suga et al.; "Measurement of in vivo local shear modulus using MR elastography multiple-phase patchwork offsets." IEEE Transactions on Biomedical Engineering 50, No. 7 (2003): pp. 908-915.

Meng Yin et al.; "Quantitative assessment of hepatic fibrosis in an animal model with magnetic resonance elastography." Magnetic Resonance in Medicine: An Official Journal of the International Society for Magnetic Resonance in Medicine 58, No. 2 (2007): pp. 1-20. US.

(Continued)

*Primary Examiner* — Keith M Raymond
*Assistant Examiner* — Ashish S. Jasani
(74) *Attorney, Agent, or Firm* — Boyle Fredrickson, S.C.

(57) ABSTRACT

A driver for transperineal magnetic resonance elastography provides a body harness stabilizing a mechanical actuator against a body reference point to provide improved imaging. The driver may employ a polymer bellows for mechanical simplicity and low cost.

21 Claims, 2 Drawing Sheets

(56) References Cited

OTHER PUBLICATIONS

Shane A. Wells et al.; "Magnetic Resonance Elastography to Identify Prostate Phenotypes of Lower Urinary Tract Symptoms"; Research Paper; pp. 1-4; US.

Ramin S. Sahebjavaher et al.; "Transperineal prostate MR elastography: initial in vivo results." Magnetic Resonance in Medicine 69, No. 2 (2013): pp. 411-420.

* cited by examiner 18
24
20
56
57
56
56
57
50
51
50

70
16
72
74
10
8 kPa
80
76
0
88
18

MAGNETIC RESONANCE ELASTOGRAPHY SYSTEM FOR THE PROSTATE

BACKGROUND OF THE INVENTION

The present invention relates generally to magnetic resonance elastography (MRE) and in particular to a passive driver adapted to generate the necessary compression waves for transperineal elastography in the prostate.

Elastography is an imaging technique that reveals tissue stiffness, providing information similar to that provided by palpation. In magnetic resonance elastography (MRE), compression waves are induced into the tissue by a mechanical driver coupled to the tissue. The induced tissue waves are then measured to yield an image indicating tissue stiffness. MRE is understood in the art and may typically use a modified phase-contrast sequence and a variety of different measurement techniques including evaluating local spatial frequency, phase gradient, direct inversion of the wave equation, and finite element based iterative methods.

MRE has been used to image the prostate using a transperineal driver to apply rapidly varying pressure to the perineum in order to produce the necessary compression waves. The transperineal driver provides a cylinder attached to a patient table with an internal movable piston driven pneumatically by a remote pressure source operating at about 45 Hz. See, Sahebjavaher, R. S., Baghani, A., Honarvar, M., Sinkus, R. and Salcudean, S. E. (2013), Transperineal prostate MR elastography: Initial in vivo results, Magn Reson Med, 69:411-420, https://doi.org/10.1002/mrm.24268, hereby incorporated by reference.

SUMMARY OF THE INVENTION

The present inventors have determined that relative movement between the driver and the patient, incidental to the controlled motion of the driver, introduces image degrading artifacts that can be addressed using a patient attached harness fixing the driver to move with the patient. A novel bellows construction further simplifies the driver making it possible to construct a disposable device for simplified clinical use.

More specifically, in one embodiment, the invention provides a driver for magnetic resonance elastography having a mechanical actuator sized to fit between a patient's legs and providing at a proximal end, an actuator head adapted to abut the patient's perineum and to apply a periodic force to the perineum at a frequency in excess of 50 Hz. An actuator support including a strap passing between legs of the patient and attaches to a body harness fixedly engaging the patient's body, biasing the actuator head against the perineum during the application of the periodic force.

It is thus a feature of at least one embodiment of the invention to provide a driver support positionally referenced against the patient's body according to the inventor's recognition that even low-frequency patient motion can produce significant degradation in the desired stiffness data.

The mechanical actuator may be a fluid chamber applying the periodic force as a function of a varying fluid pressure in the fluid chamber; and the driver may further including an electromechanical fluid pump producing the varying pressure at an outlet communicating with the fluid chamber by means of a flexible hose, wherein the fluid chamber and hose are electrically nonconductive.

It is thus a feature of at least one embodiment of the invention to provide an MRI compatible mechanical actuator providing a low-cost and hence disposable patient contacting portions.

The mechanical actuator may communicate with an electromagnetic pneumatic pump to provide the varying fluid pressure by means of pumped air.

It is thus a feature of at least one embodiment of the invention to provide a mechanical coupling that eliminates potential liquid fluid spilling and that provides reduced mass inertia for higher vibration speeds.

The fluid chamber may be a bellows having circumferential pleats to expand principally along a single axis favoring a flexing of the material of the bellows over a stretching of the material of the bellows.

It is thus a feature of at least one embodiment of the invention to provide a fluid chamber whose expansion can be largely constrained to a single axis to reduce the necessary volume and potentially increase the actuation frequency possible with a remote pump without the need for rigid cylinder and piston.

The bellows may be substantially radially symmetric about the single axis.

It is thus a feature of at least one embodiment of the invention to provide a bellows shape that resists radial expansion through hoop circumferential forces developed in a relatively inelastic bellows material thereby promoting axial expansion.

The actuator head of the mechanical actuator may be elastically biased with respect to the patient's body against the perineum by the actuator support.

It is thus a feature of at least one embodiment of the invention to provide a biasing of the actuator with respect to the patient's body to minimize changes in steady-state force with patient motion while ensuring good contact and pressure coupling with the perineum.

The body harness may be a waist strap fitting about the patient's waist to resist axial motion.

It is thus a feature of at least one embodiment of the invention to minimize strap length and harness size through the use of a waste strap that can be stabilized by the patient's hip bones.

The strap may provide a single fabric panel extending forwardly through the patient's legs over a portion of the abdomen to attach to the waist strap at a proximal end and to the mechanical actuator at a distal end.

It is thus a feature of at least one embodiment of the invention to improve patient comfort and privacy through the use of a supporting fabric panel.

The strap may be bifurcated to extend rearwardly through the patient's legs with increasing lateral separation before attaching to the waist strap.

It is thus a feature of at least one embodiment of the invention to improve lateral stability and comfort in the harness.

These particular objects and advantages may apply to only some embodiments falling within the claims and thus do not define the scope of the invention.

DETAILED DESCRIPTION OF THE PREFERRED EMBODIMENT

Figure 1:
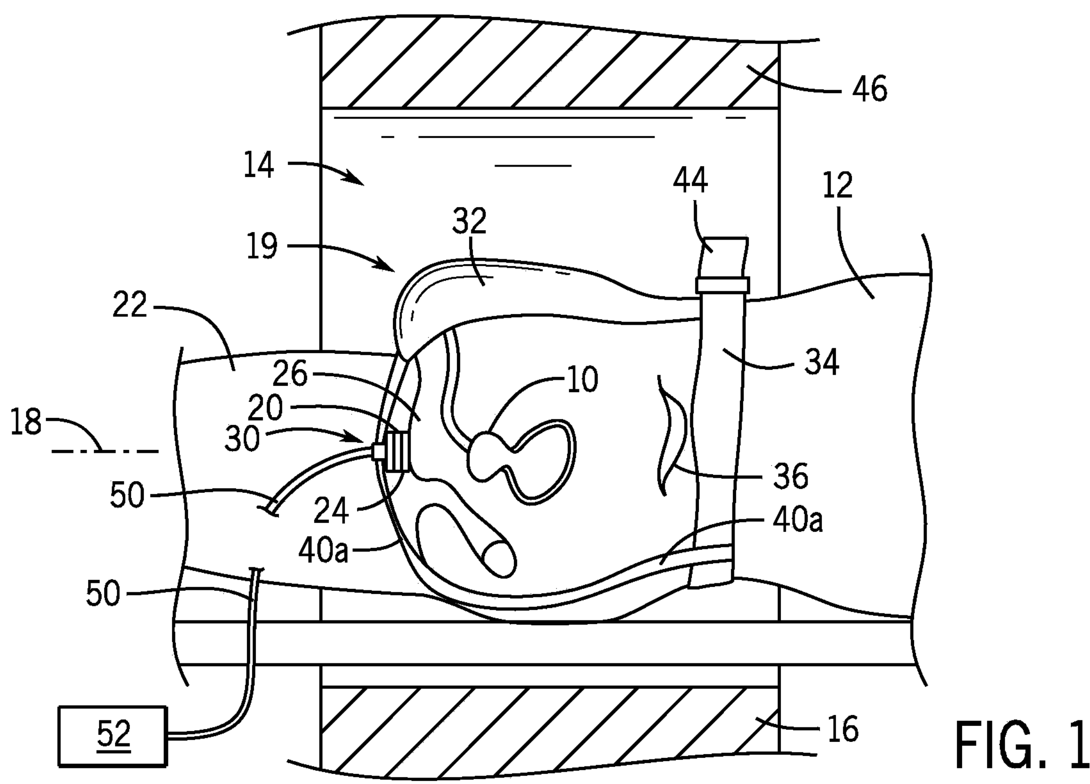
FIG. 1 is a fragmentary, partial elevational cross-section of a patient in a supine position within an MRI machine bore showing positioning of a mechanical actuator per one embodiment of the present invention against the perineum using a patient stabilized harness.
Figure 2:
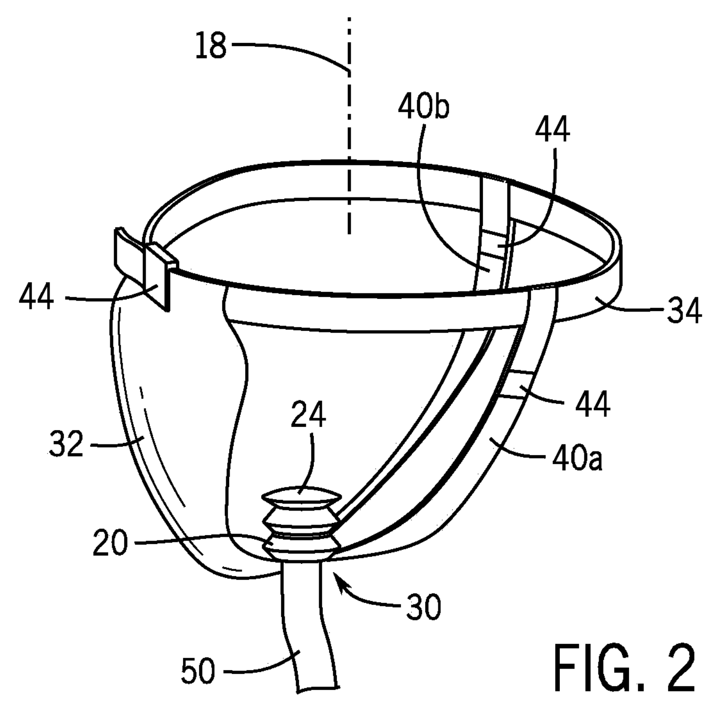
FIG. 2 is a perspective view of the harness and actuator of FIG. 1 showing a front extending cloth panel attached at a distal end of the actuator and also to two rearwardly and laterally extending elastic straps.

Referring now to FIG. 1, magnetic resonance elastography (MRE) images may be obtained of a prostate 10 of a patient 12, with the patient 12 positioned in a supine orientation within a bore 14 of a magnetic resonance machine 16. As so positioned, the patient's superior-inferior axis 18 of the patient 12 will typically be aligned with the axis of the bore 14.

In order to provide the necessary compression waves for MRE, a driver assembly 19 may be applied to the patient so that a mechanical actuator 20 of the driver assembly 19 is received between the patient's legs 22 having an actuator head 24 abutting the perineum 26. As so fit, the actuator head 24 applies a force generally aligned with axis 18 producing compression waves (not shown) transmitted through the body to the prostate 10.

A distal end 30 of the mechanical actuator 20, spaced from the actuator head 24 along the axis 18, may be attached to an actuator support providing an anteriorly extending fabric panel 32 providing a cup operating in the manner of an athletic supporter, the fabric panel 32 extending from the distal end 30 of the mechanical actuator 20 to a waistband 34. The waistband 34 passes around the patient's waist above the ilium 36 to resist displacement along the axis 18 with respect to the patient. The waistband 34 may include a length adjuster 44, for example, a belt buckle or cinch of a type known in the art, or elastic, to firmly engage the patient 12 and may include internal padding both for this purpose and comfort.

The inferior portion of the fabric panel 32 extending between the patient's legs and attached to the distal end 30 of the mechanical actuator 20 also attaches to two straps 40*a* and 40*b* extending from the distal and 30 posteriorly and superiorly while separating laterally apart before attaching to a posterior portion of the waistband 34 at separate laterally displaced locations.

Fabric panel 32 and straps 40 may be an elastic material to permit a preloading of a force on the mechanical actuator 20 with a superior bias and may also include length adjusters 44, for example, implemented by means of hook and loop type overlapping sections or the like.

The mechanical actuator 20 may provide an expanding pneumatic chamber communicating by means of a hose 50 and coupling 51 with a pump 52 capable of providing a varied air pressure to the actuator 20 at a rate in excess of 50 Hz and desirably in excess of 100 Hz or in excess of 300 Hz but less than 600 Hz. The pump 52, in one embodiment, may be a commercially available active driver manufactured by Resoundant Inc. of Rochester, Minnesota USA for MRE.

Figures 3, 4:
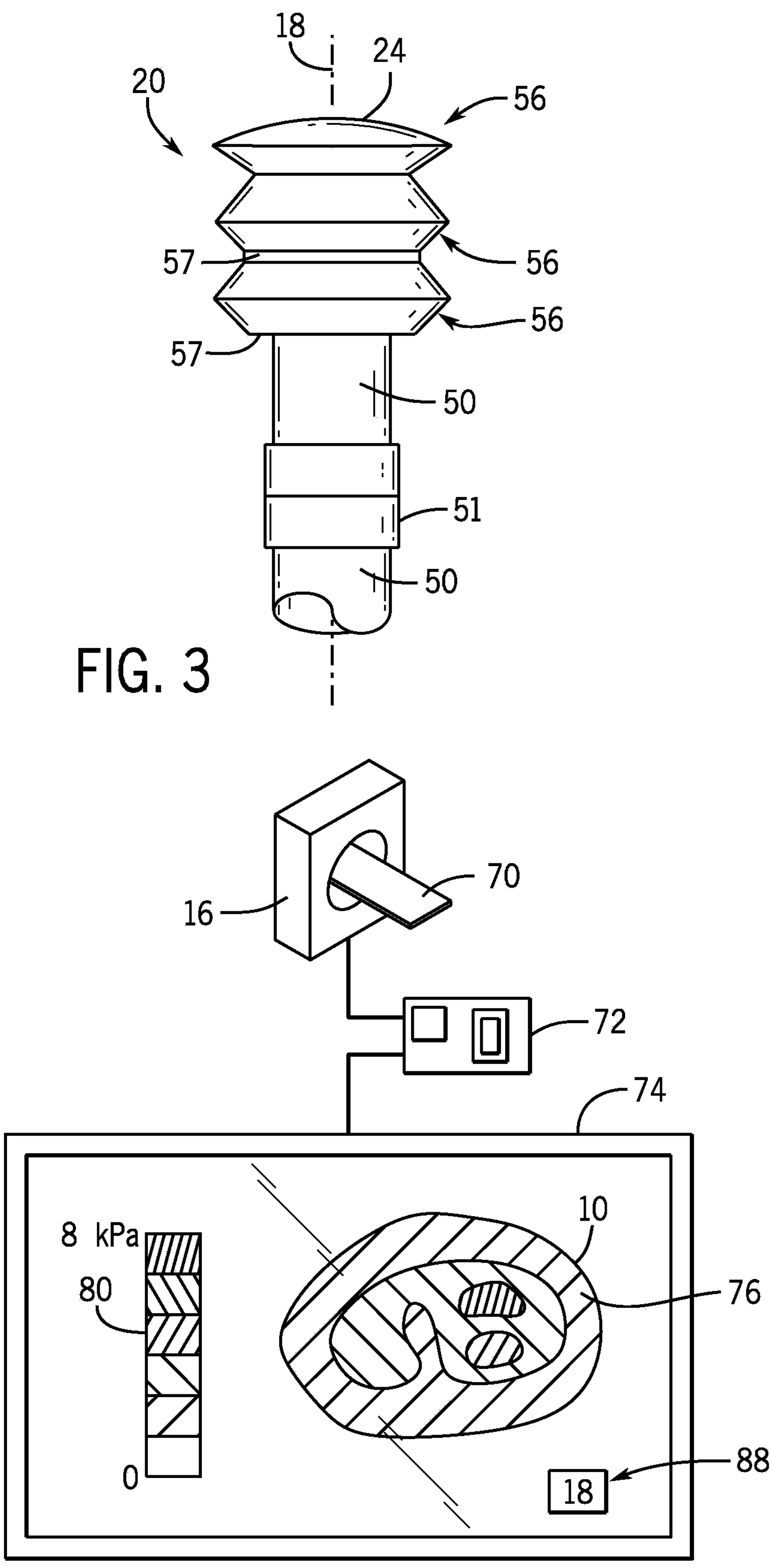
FIG. 3 is a side elevational view of the bellows showing the pleat structure.
FIG. 4 is an example display produced by MRI machine showing a false color depiction of prostate stiffness.

Referring now to FIG. 3, the pneumatic chamber of the mechanical actuator may be in the form of a bellows 56 constructed of a flexible polymer such as low density polyethylene providing a volume of approximately 30 mL. The bellows 56 may be characterized by multiple circular circumferential pleats 54 concentric about axis 18 when properly positioned. The pleats allow expansion of the bellows along the axis 18 by flexing of the pleats at creases without substantial stretching of the wall materials outside creases to allow expansion to be concentrated along axis 18 rather than in radial stretching of the material or deformation.

The hose 50 is desirably close to the average diameter of the bellows 56 (in one nonlimiting example, plus or minus 20%) for improved high frequency response and reduced frictional energy dissipation.

An actuator head 24 of the bellows 56 may provide for a shaped surface to better couple acoustically with the perineum and may include an elastomeric coating for comfort. In one embodiment, MRI visible markers are placed on the mechanical actuator 20 in order to allow confirmation of its location during the imaging process. In this regard, the actuator head 24 may incorporate an MRI contrast material such as small non-ferromagnetic metal spheres, coils, cylinders, etc in an elastomeric or polymer material. In addition, a marker ring 57 or individual beads or other fiducial markers may be located on the actuator 20, displaced from the actuator head 24 to also help confirm the proper placement, movement, and orientation of the actuator head 24. Additional supporting ribs 57 may be applied to the distal end of the bellows 56 to reduce flexure at this and During application of a periodic vibration to the perineum by means of the varied pressure described above, multi-parametric magnetic resonance imaging (mpMRE) of the prostate may be conducted including parametric magnetic resonance imaging (pMRE), for example, using an MRI machine commercially available, for example, from GE Healthcare of Wisconsin US under the trade name 3.0 T Premier. This imaging may be performed with the patient 12 in the supine position, as mentioned above, using an integrated body coil and anterior 32-channel array coil also commercially available from GE Healthcare under the trade name Air Acquisitions. The acquired images may include axial, sagittal and coronal T2 TSE, axial diffusion weighted imaging (DWI) (b800 and b1500 or higher) from which apparent diffusion coefficient (ADC) maps, T1 and/or T2 mapping, axial pre- and dynamic post-contrast enhancement (DCE) T1 FSPGR may be obtained.

In one nonlimiting example, imaging may be conducted at 90 and 100 Hz vibration frequencies with the following parameters: FOV=30 cm, TE/TR=57.6-74.0 ms/1600 ms, flip angle=90, slices=18, slice thickness=2.9 mm, slice gap=0, matrix=96×96, BW=256 Hz, averages=1, acceleration=2. Wave images may then be processed with a 3D direct-inversion algorithm. Three quantitative parametric maps for viscoelastic properties may then be generated: complex shear modulus (1G*1), storage modulus (G') and loss modulus (G"). The damping ratio ($\xi$=G"/2G') may be calculated.

Referring now to FIG. 4, the magnetic resonance imaging machine 16 such as that described above may provide a patient table 70 for receiving the supine patient 12 (not shown), the patient wearing the driver assembly 19 discussed above for imaging during compression wave generation. Data from the radiofrequency coils of the magnetic resonance imaging machine 16 are processed by electronic computer 72 using the procedures described above. The electronic computer 72 may include one or more processors together with electronic memory holding a stored program for this purpose. The electronic computer 72 may communicate with a display screen 74 to provide a false color image 76, for example, of a slice through the prostate with various colors matching by means of a scale 80 to tissue stiffness values, for example, between zero and twelve kPa. Prostate volume 88 may also be calculated and shown. Desirably, a color mapping range (shown here as 0-12 kPa) may be flexibly set by the user to accentuate desired elasticity ranges. The elasticity of the tissue of the prostate may further be characterized with respect to the storage modulus (elastic modulus) representing the amount of energy stored in the elasticity of the tissue, the loss modulus (viscous modulus) representing the energy dissipated through viscosity, and the damping ratio generally reflecting the ratio of the loss modulus to the storage modulus.

The acquired MRI data may further be used to provide each or any of: prostatic urethral length, bladder wall mass, and post void residual through manual or automatic segmentation, such as may be useful for diagnostic purposes.

Certain terminology is used herein for purposes of reference only, and thus is not intended to be limiting. For example, terms such as "upper", "lower", "above", and "below" refer to directions in the drawings to which reference is made. Terms such as "front", "back", "rear", "bottom" and "side", describe the orientation of portions of the component within a consistent but arbitrary frame of reference which is made clear by reference to the text and the associated drawings describing the component under discussion. Such terminology may include the words specifically mentioned above, derivatives thereof, and words of similar import. Similarly, the terms "first", "second" and other such numerical terms referring to structures do not imply a sequence or order unless clearly indicated by the context.

When introducing elements or features of the present disclosure and the exemplary embodiments, the articles "a", "an", "the" and "said" are intended to mean that there are one or more of such elements or features. The terms "comprising", "including" and "having" are intended to be inclusive and mean that there may be additional elements or features other than those specifically noted. It is further to be understood that the method steps, processes, and operations described herein are not to be construed as necessarily requiring their performance in the particular order discussed or illustrated, unless specifically identified as an order of performance. It is also to be understood that additional or alternative steps may be employed.

References to "a microprocessor" and "a processor" or "the microprocessor" and "the processor," can be understood to include one or more microprocessors that can communicate in a stand-alone and/or a distributed environment(s), and can thus be configured to communicate via wired or wireless communications with other processors, where such one or more processor can be configured to operate on one or more processor-controlled devices that can be similar or different devices. Furthermore, references to memory, unless otherwise specified, can include one or more processor-readable and accessible memory elements and/or components that can be internal to the processor-controlled device, external to the processor-controlled device, and can be accessed via a wired or wireless network.

It is specifically intended that the present invention not be limited to the embodiments and illustrations contained herein and the claims should be understood to include modified forms of those embodiments including portions of the embodiments and combinations of elements of different embodiments as come within the scope of the following claims. All of the publications described herein, including patents and non-patent publications, are hereby incorporated herein by reference in their entireties.

To aid the Patent Office and any readers of any patent issued on this application in interpreting the claims appended hereto, applicants wish to note that they do not intend any of the appended claims or claim elements to invoke 35 U.S.C. 112(f) unless the words "means for" or "step for" are explicitly used in the particular claim.

What we claim is:

1. A driver for magnetic resonance elastography comprising a mechanical actuator sized to fit between a patient's legs having at a proximal end, an actuator head adapted to abut the patient's perineum to apply a periodic force to the perineum at a frequency in excess of 50 Hz and sidewalls extending distally from the actuator head;

an actuator support including a strap passing between legs of the patient and attached to a body harness fixedly engaging the patient's body, the strap and body harness cooperating to position and bias the actuator head against the perineum during an application of the periodic force;

wherein the mechanical actuator is a bellows with a fluid chamber having one end adapted to directly contact the patient's perineum and apply the periodic force as a function of a varying fluid pressure in the fluid chamber; and wherein a material of the sidewalls is formed with multiple circumferential pleats adapted to flex with the periodic force, and wherein the sidewalls are adapted to expand preferentially in an axial direction primarily by flexing of the pleats rather than elastic expansion of the material of the bellows toward the perineum relative to a radial direction perpendicular to the axial direction.

2. The driver of claim 1 further including an electromechanical fluid pump producing the varying pressure at an outlet communicating with the fluid chamber by means of a flexible hose, wherein the fluid chamber and hose are electrically nonconductive.

3. The driver of claim 2 further including electromagnetic pneumatic pump communicating with the flexible hose to provide the varying fluid pressure by means of pumped air.

4. The driver of claim 2 wherein the fluid chamber is a bellows providing circumferential pleats to expand principally along a single axis favoring a flexing of a material of the bellows over a stretching of the material of the bellows.

5. The driver of claim 4 wherein the bellows is substantially radially symmetric about the single axis.

6. The driver of claim 1 wherein the actuator head of the mechanical actuator is elastically biased with respect to the patient's body against the perineum by the actuator support.

7. The driver of claim 1 wherein the body harness is a waist strap adapted to fit about a patient's waist and including a length adjuster positioned between the waist strap and the mechanical actuator and adapted to adjust a relaxed length of the waist strap to firmly engage the patient's waist above the ilium.

8. The driver of claim 7 wherein the strap provides a single fabric panel extending forwardly through the patient's legs over a portion of the patient's abdomen to attach to the waist strap at a proximal end and to the mechanical actuator at a distal end.

9. The driver of claim 7 wherein the strap is bifurcated to extend rearwardly through the patient's legs with increasing lateral separation before attaching to the waist strap.

10. The apparatus of claim 1 wherein the actuator head is adapted to abut the patient's perineum to apply a periodic force to the perineum at a frequency in excess of 300 Hz for MRI for elastography imaging.

11. The apparatus of claim 1 further including an air hose connecting the actuator to a pump providing varied air pressure at a rate in excess of 50 Hz and wherein a diameter of the air hose is within 20% of the average diameter of the bellows.

12. A method of prostate magnetic resonance elastography comprising:

positioning a mechanical actuator having an actuator head at its proximal end so that the actuator head abuts a patient's perineum by attaching an actuator support to the patient, the actuator support having a strap passing between legs of the patient and attached to a body harness fixedly engaging the patient's body and biasing actuator head against the perineum;

applying a periodic force with the mechanical actuator to the perineum at a frequency in excess of 50 Hz; and imaging wave motion in the prostate motion during an application of the periodic force to provide an image revealing tissue stiffness in the prostate;

wherein the mechanical actuator is a bellows with a fluid chamber having one end adapted to directly contact the patient's perineum and apply the periodic force as a function of a varying fluid pressure in the fluid chamber; and wherein a material of the sidewalls is formed with multiple circumferential pleats adapted to flex with the periodic force, and wherein the sidewalls are adapted to expand preferentially in an axial direction primarily by flexing of the pleats rather than elastic expansion of the material of the bellows toward the perineum relative to a radial direction perpendicular to the axial direction.

13. The method of claim 12 further including attaching an electromechanical fluid pump producing the varying pressure at an outlet to the fluid chamber by means of a flexible hose, wherein the fluid chamber and hose are electrically nonconductive.

14. The method of claim 13 wherein the varying fluid pressure is air pressure.

15. The method of claim 13 wherein the fluid chamber is a bellows providing circumferential pleats to expand principally along a single axis favoring a flexing of a material of the bellows over a stretching of the material of the bellows.

16. The method of claim 15 wherein the bellows is substantially radially symmetric about the single axis.

17. The method of claim 12 wherein the actuator head of the mechanical actuator is elastically biased with respect to the patient's body against the perineum by the actuator support.

18. The method of claim 12 wherein the body harness is a waist strap adapted to fit and be retained about a patient's waist and including a length adjuster adapted to adjust a relaxed length of the waist strap to firmly engage the patient's waist above the ilium.

19. The method of claim 18 wherein the strap provides a single fabric panel extending forwardly through the patient's legs over a portion of the patient's abdomen to attach to the waist strap at a proximal end and to the mechanical actuator at a distal end.

20. The method of claim 18 wherein the strap is bifurcated to extend rearwardly through the patient's legs with increasing lateral separation before attaching to the waist strap.

21. The method of claim 12 wherein the stiffness is characterized in terms selected from the group consisting of energy storage, energy loss, and damping ratio.

* * * * *